(12) United States Patent
Itakura et al.

(10) Patent No.: US 6,689,745 B1
(45) Date of Patent: Feb. 10, 2004

(54) AGENT FOR AMELIORATING PANCREATIC FUNCTION DISORDER

(75) Inventors: Yasushi Itakura, Nara-ken (JP); Mutsuo Taiji, Takatsuki (JP)

(73) Assignee: Sumitomo Pharmaceuticals Company, Limited, Osaka (JP)

( * ) Notice: Subject to any disclaimer, the term of this patent is extended or adjusted under 35 U.S.C. 154(b) by 0 days.

(21) Appl. No.: 09/958,738

(22) PCT Filed: Apr. 7, 2000

(86) PCT No.: PCT/JP00/02264

§ 371 (c)(1), (2), (4) Date: Oct. 16, 2001

(87) PCT Pub. No.: WO00/62796

PCT Pub. Date: Oct. 26, 2000

(30) Foreign Application Priority Data

Apr. 16, 1999 (JP) ............................................. 11/109602

(51) Int. Cl.⁷ ...................... A61K 38/00; A61K 38/16; C07K 5/00; C07K 38/16
(52) U.S. Cl. ...................... 514/2; 424/198.1; 530/350; 530/399; 530/388.22
(58) Field of Search .......................... 514/2; 530/388.22, 530/351, 350, 399; 424/130.1, 198.1; 435/7.1

(56) References Cited

PUBLICATIONS

Ono, et al, (1997) Biochem. Biophys. Res. Comm., 238: 633–637.*

Polak M, et al., Nerve growth factor induces neuron–like differentiation of an insulin–secreting pancreatic beta cell line. Proc. Natl. Acad. Sci USA, 1993 vol. 90, No. 12, pp5781–5785.

Ono M. et al., "Brain–derived neurotrophic factor reduces blood glucose level in obese diabetic mice but not in normal mice" Biochem. Biophys. Res. Commun., 1997, vol. 238, No. 2, pp. 633–637.

Tazi, A. et al., "Neurotrophin–3 increases intracellular calcium in a rat insulin–secreting cell line through its action on a functional TrkC receptor" J. Biol. Chem., 1996, vol. 271, No. 17, pp. 10154–10160.

Shibayama E., et al., "Cellular localization of the Trk neurotrophin receptor family in human non–neuronal tissues" Am. J. Pathol., 1996, vol. 148, No. 6, pp. 1807–1818.

Rosenbaum, T., et al., "Pancreatic beta cells synthesize and secrete nerve growth factor" Proc. Natl. Acad. Sci. USA, 1998, vol. 95, No. 13, pp 7784–7788.

Ono et al., Biochemical & Biophysical Research Communications, vol. 238, pp. 633–637, (1997).

Polak et al., Proc. Natl. Acad. Sci. USA, vol. 90, pp. 5781–5785, (1993).

* cited by examiner

Primary Examiner—Elizabeth Kemmerer
Assistant Examiner—Sandra Wegert
(74) Attorney, Agent, or Firm—Birch, Stewart, Kolasch & Birch, LLP

(57) ABSTRACT

Agents for protecting or ameliorating pancreatic cells and tissues which contains as the active ingredient a neurotrophic factor such as BDNF. By using these drugs, degenerative dropout of pancreatic cells and pancreatic hypofunction caused by diabetes, acute/chronic pancreatitis, etc. can be efficaciously prevented and treated.

8 Claims, 7 Drawing Sheets db/db          db/db          db/m
(vehicle)      (BDNF)         (normal)

AGENT FOR AMELIORATING PANCREATIC FUNCTION DISORDER

This application is the national phase under 35 U.S.C. §371 of PCT International Application No. PCT/JP00/02264 which has an International filing date of Apr. 7, 2000, which designated the United States of America and was not published in English.

TECHNICAL FIELD

The present invention relates to an agent for protecting pancreatic cells or an agent for ameliorating hypofunction of pancreatic cells, or an agent for protecting pancreatic tissues or an agent for ameliorating hypofunction of pancreatic tissues, these agent comprising as the active ingredient a neurotrophic factor.

BACKGROUND ART

Pancreas is an organ consisting of the endocrine gland tissues called pancreatic islet (Langerhans islet) and the exocrine gland tissues secreting digestive enzymes such as amylase, lipase, protease, etc. In the Langerhans islet, B cells (β cells) synthesizing and secreting insulin, etc., A cells (α cell) synthesizing and secreting glucagon, etc., D cells (δ cells) synthesizing and secreting somatostatin, and pancreatic polypeptide cells (hereinafter, referred to as PP cells) synthesizing and secreting pancreatic polypeptide, etc. exist, and they greatly affect the control of blood glucose and metabolism. Disorders of these endocrine glands and exocrine glands may induce abnormalities of controlling blood glucose level (e.g., diabetes mellitus, hypoglycemia, insulin shock, etc.) and decreased digestion (e.g., steatorrhea, etc.), respectively.

Pancreatic function disorders are induced by various causes, and representative underlying diseases thereof are, for example, pancreatitis or diabetes mellitus. Pancreatitis is clinically classified into acute pancreatitis and chronic pancreatitis, and the former is mono-pancreatitis or repetitive pancreatitis being characterized by acute bellyache attack accompanied by increase in pancreatic enzyme level in blood or urine. Serious acute pancreatitis further induces necrosis and hemorrhage of pancreatic substratum, serious renal failure, or respiratory failure, and may results in shock to death. The treatment thereof is usually carried out by inhibiting pancreatic exocrine by fasting and an H2 blocker, and further by preventing complications by administering a protease inhibitor, an antibiotic, or an analgesic.

Chronic pancreatitis is mainly induced by over-uptake of alcohol, and characterized by repetitive or persistent bellyache. Morphologically, it is characterized by immethodical sclerosis accompanied by destruction and permanent dissipation of pancreatic exocrine tissues, and it induces symptoms caused by pancreatic exocrine grand failure such as steatorrhea. In chronic pancreatitis, it is observed that about 50% of the patients produce a complication of diabetes mellitus due to pancreatic endocrine disorder (pancreatic diabetes). The characteristic of the secondary diabetes of this chronic pancreatitis is the lack of both insulin and glucagon, and the treatment thereof is mostly carried out by administration of insulin. About half of the causes of death for chronic pancreatitis are concerned with diabetes mellitus, and hypoglycemia after insulin injection (i.e., insulin shock) caused by the lack of glucagon or diabetic complications such as nephropathy or infections are pointed out as a cause of death.

In addition, sulfonylurea derivatives having an insulin secretion promoting activity have been used in the treatment of diabetes mellitus, but they may occasionally induce pancreatic cell dysfunction or pancreatic tissue dysfunction, due to excessive burden on the pancreas by forcing the pancreas to secrete insulin.

At present, a method for promoting a spontaneous recovery of pancreatic function has been used in the treatment of pancreatic function disorder, by eliminating diseases or factors that are a cause therefor (cf., "Learning of Pancreatopathy", edited by Tadashi TAKEUCHI, published by Nankodo Co. Ltd., Aug. 1, 1993), but there in have not been known or used any method or agent for aggressively recovering the decreased pancreatic function.

On the other hand, neurotrophic factors are a generic name for proteins, which are provided from target cells or neurons and glia cells and Schwann cells in the living body. They show activities of maintaining the survival and differentiation of neurons, and are classified into many types according to the kinds of nerves or receptors to function. Among them, proteins being known as neurotrophins have high structural homology with each other and form a family. The typical examples thereof are neurotrophins such as nerve growth factor (hereinafter, abbreviated as NGF), brain-derived neurotrophic factor (hereinafter, abbreviated as BDNF), neurotrophin 3 (hereinafter, abbreviated as NT-3), neurotrophin 4 (hereinafter, abbreviated as NT-4), neurotrophin 5 (hereinafter, abbreviated as NT-5), or neurotrophin 6 (NT-6); ciliary neurotrophic factor (hereinafter, abbreviated as CNTF); glia cell-derived neurotrophic factor (hereinafter, abbreviated as GDNF), etc. In addition, neurotrophins are known to act as a specific ligand of receptors (trkA, trkB and/or trkC), which are the products of p-75 and trk genes (cf. Takeshi NONOMURA, Hiroshi HATANAKA; Jikken Igaku, vol. 13, p. 376 (1995)).

Neurotrophic factors have been studied with respect to their medical use as a therapeutic agent for treating a patient of neurodegenerative diseases. For example, Society for Neuroscience, vol. 21, p. 1535 (1995), A. P. Mizisin et al. discloses the pharmacological activity of BDNF on diabetic peripheral neuropathy, but this literature merely suggests the possible pharmacological activity of BDNF on neuropathy based on the finding that BDNF improves the reduction of motor nerve conduction in vivo. WO 98/32458 discloses that neurotrophic factors such as BDNF can normalize the blood glucose level of diabetic animal models, and applications thereof onto the treatment of diabetes mellitus are disclosed therein.

DISCLOSURE OF INVENTION

As mentioned above, an agent for protecting pancreatic cells or an agent for ameliorating damaged pancreatic cells, an agent for protecting pancreatic cell function or an agent for ameliorating pancreatic cell hypofunction, or an agent for protecting pancreatic tissues or an agent for ameliorating damaged pancreatic tissues, or an agent for protecting pancreatic tissue function or an agent for ameliorating pancreatic tissue hypofunction has been desired in the medical field.

The present inventors have an interest in that the insulin secretion of BDNF-treated type 2 diabetic animal models is kept at high level, and have studied pancreatic function ameliorating activities by using type 2 diabetic animal models. As a result, they have found that BDNF can (1) increase the decreased insulin content in pancreas of type 2 diabetes animal models, (2) reduce the increased glucagon content in pancreas, (3) normalize the localization of A cells and D cells in the pancreatic Langerhans islet, (4) promote the re-granulation of insulin secretory granules of B cells in the pancreatic Langerhans islet, and normalize the organellae. Based on the finding of these pancreatic function ameliorating activity and pancreatic cell protecting activity of BDNF, the present inventors have further studied and have accomplished the present invention.

More particular, the present invention relates to the following:

1. An agent for protecting pancreatic cells or an agent for ameliorating damaged pancreatic cells, which comprises as the active ingredient a neurotrophic factor;
2. An agent for protecting pancreatic cell function or an agent for ameliorating pancreatic cell hypofunction, which comprises as the active ingredient a neurotrophic factor;
3. An agent for protecting pancreatic tissues or an agent for ameliorating damaged pancreatic tissues, which comprises as the active ingredient a neurotrophic factor;
4. An agent for protecting pancreatic tissue function or an agent for ameliorating pancreatic tissue hypofunction, which comprises as the active ingredient a neurotrophic factor;
5. The agent for protection or amelioration of the function according to the above 1 or 2, wherein the pancreatic cell is B cells ($\beta$ cells), A cells ($\alpha$ cells), and/or D cells ($\delta$ cells) of the pancreatic Langerhans islet;
6. The agent for protection or amelioration of the function according to the above 1 or 2, wherein the pancreatic cell is B cells ($\beta$ cells), A cells ($\alpha$ cells), D cells ($\delta$ cells), and/or PP cells of the pancreatic Langerhans islet;
7. The agent for protecting pancreatic tissue function or the agent for ameliorating hypofunction of pancreatic tissue according to the above 3 or 4, wherein the pancreatic tissue is the pancreatic Langerhans islet;
8. The agent for protection or amelioration according to the above 1, 2, 5 or 6, which is an agent for protecting or ameliorating pancreatic endocrine function (insulin secretion ability, glucagon secretion ability and/or somatostatin secretion ability) or an agent for ameliorating pancreatic endocrine function disorder (insulin secretion ability, glucagon secretion ability and/or somatostatin secretion ability);
9. The agent for protection or amelioration according to the above 3, 4 or 7, which is an agent for protecting or ameliorating pancreatic endocrine function (insulin secretion ability, glucagon secretion ability and/or somatostatin secretion ability) or an agent for ameliorating pancreatic endocrine function disorder (insulin secretion ability, glucagon secretion ability and/or somatostatin secretion ability);
10. The agent for protection or amelioration according to the above 1, 2, 5, 6, or 8, wherein the cause for hypofunction or disorder of pancreatic cells is diabetes mellitus;
11. The agent for protection or amelioration according to the above 3, 4, 7 or 9, wherein the cause for hypofunction or disorder of pancreatic tissues is diabetes mellitus;
12. The agent for protection or amelioration according to the above 1, 2, 5, 6, or 8, wherein the cause for hypofunction or disorder of pancreatic cells is acute pancreatitis or chronic pancreatitis;
13. The agent for protection or amelioration according to the above 3, 4, 7 or 9, wherein the cause for hypofunction or disorder of pancreatic tissues is acute pancreatitis or chronic pancreatitis;
14. The agent for protection or amelioration according to the above 1, 2, 5, 6, or 8, wherein the cause for hypofunction or disorder of pancreatic cells is a sulfonylurea derivative;
15. The agent for protection or amelioration according to the above 3, 4, 7 or 9, wherein the cause for hypofunction or disorder of pancreatic tissues is a sulfonylurea derivative;
16. An agent for treating acute pancreatitis or chronic pancreatitis, which comprises as the active ingredient the agent for protection or amelioration as set forth in any one of the above 1, 2, 5, 6, and 8;
17. An agent for treating acute pancreatitis or chronic pancreatitis, which comprises as the active ingredient the agent for protection or amelioration as set forth in any one of the above 3, 4, 7 and 9;
16. An agent for protecting pancreatic endocrine tissues or an agent for ameliorating damaged pancreatic endocrine tissues, which comprises as the active ingredient a neurotrophic factor;
17. An agent for protecting pancreatic endocrine tissue function or an agent for ameliorating hypofunction of pancreatic endocrine tissues, which comprises as the active ingredient a neurotrophic factor;
18. An agent for protecting pancreatic exocrine tissues or an agent for ameliorating damaged pancreatic exocrine tissues, which comprises as the active ingredient a neurotrophic factor;
19. An agent for protecting pancreatic exocrine tissue function or an agent for ameliorating hypofunction of pancreatic exocrine tissues, which comprises as the active ingredient a neurotrophic factor;
20. The agent for protection or amelioration according to any one of the above 1 to 19, wherein the neurotrophic factor of the active ingredient is NGF (nerve growth factor), BDNF (brain-derived neurotrophic factor), CNTF (ciliary neurotrophic factor), NT-3 (neurotrophin 3), NT-4 (neurotrophin 4), NT-5 (neurotrophin 5), or NT-6 (neurotrophin 6);
21. The agent for protection or amelioration according to any one of the above 1 to 19, wherein the neurotrophic factor of the active ingredient is BDNF (brain-derived neurotrophic factor);
22. The agent for protection or amelioration according to any one of the above 1 to 19, wherein the neurotrophic factor of the active ingredient is CNTF (ciliary neurotrophic factor);
23. The agent for protection or amelioration according to any one of the above 1 to 19, wherein the neurotrophic factor of the active ingredient is NT-3 (neurotrophin 3);
24. The agent for protection or amelioration according to any one of the above 1 to 19, wherein the neurotrophic factor of the active ingredient is NT-4 (neurotrophin 4);
25. The agent for protection or amelioration according to any one of the above 1 to 19, wherein the neurotrophic factor of the active ingredient is NT-5 (neurotrophin 5);
26. The agent for protection or amelioration according to any one of the above 1 to 19, wherein the neurotrophic factor of the active ingredient is NT-6 (neurotrophin 6);
27. The agent for protection or amelioration according to any one of the above 1 to 19, wherein the neurotrophic factor of the active ingredient is NGF (nerve growth factor);

28. The agent for protection or amelioration according to any one of the above 1 to 19, wherein the neurotrophic factor of the active ingredient is GDNF (glia cell-derived neurotrophic factor);

29. The agent for protection or amelioration according to any one of the above 1 to 19, wherein the neurotrophic factor of the active ingredient is a trkA, a trkB and/or a trkC receptor agonist;

The meaning or definition of each term used in the present specification is explained below.

The "agent for protection" means an agent for preventing disorder or hypofunction.

The "agent for amelioration" means an agent for adjusting a damaged condition or a condition of hypofunction to the normal condition or normalizing it.

The "neurotrophic factor" means a physiologically active substance, which is secreted from the target cells for nerve growth, or by autocrine or paracrine, and promotes the growth, differentiation, or survival of neurons to form a neural circuit (synapse) in the living body. For example, the neurotrophic factor includes neurotrophins such as a nerve growth factor (hereinafter, abbreviated as NGF), a brain-derived neurotrophic factor (hereinafter, abbreviated as BDNF), a neurotrophin 3 (hereinafter, abbreviated as NT-3), a neurotrophin 4 (hereinafter, abbreviated as NT-4), a neurotrophin 5 (hereinafter, abbreviated as NT-5), and a neurotrophin 6 (hereinafter, abbreviated as NT-6); ciliary neurotrophic factor (hereinafter, abbreviated as CNTF); glia cell-derived neurotrophic factor (hereinafter, abbreviated as GDNF), etc. In addition, a modified recombinant neurotrophic factor produced by a substitution, a deletion, or an addition of a part of amino acid sequence of the naturally occurred neurotrophic factor sequence by a conventional technique may be included in the neurotrophic factor of the present specification, as far as it exhibits the similar physiological activity.

The "pancreatic function disorder" means pathologies, wherein the endocrine gland function or exocrine gland function of the pancreas is decreased or abnormally elevated. The endocrine gland function mainly means the secretion ability of insulin, glucagon and/or somatostatin, and the exocrine gland function mainly means the secretion ability of digestive enzymes (amylase, protease and/or lipase) into pancreatic juice. These secretion abilities can be evaluated by a conventional method being widely used in the clinical field, for example by measuring blood insulin level.

The "protection of pancreatic cells" means an action of protecting pancreatic endocrine gland cells and exocrine gland cells from degeneration induced by various causes, and it can be evaluated by examination of pancreatic tissue section under a microscope. Endocrine gland cells can specifically be stained by a conventional cell staining such as aldehyde fuchsin stain, and in the pancreatic Langerhans islet, B cells (β cells) can be stained by insulin immune staining, and A cells (α cells) can be stained by glucagon immune staining, and D cells (δ cells) can be stained by somatostatin immune staining, and the stained patterns thereof can be observed. In addition, the structure of organellae can be examined by electron microscopy for evaluation.

The "protection of pancreatic tissues" means an action of protecting pancreatic endocrine gland tissues and exocrine gland tissues from degeneration induced by various causes, and it can be evaluated by examination of pancreatic tissue section under a microscope. The stained pattern of the tissues can be examined by a conventional cell straining such as hematoxylin-eosin stain, aldehyde fuchsin stain, etc. In addition, the structure of organellae can be examined by electron microscopy for evaluation.

The "trkA, trkB and/or trkC receptor agonist" is a generic name for substances that are bound to trkA, trkB or trkC, which is among the trk gene expression products being known as receptors for "neurotrophin", and activate them to exhibit their activities. Concretely, the known neurotrophin is, for example, NGF binding to trkA, BDNF and NT-4 binding to trkB, and NT-3 binding to trkC, etc. This concept includes not only modified neurotrophins (modified by amino acid substitution, deletion or addition or sugar chain modification), but also peptides and organic compounds of a lower molecular weight as far as they exhibit a binding ability and activating ability to trkA, trkB or trkC receptor, for example, phosphorilating activity of tyrosine residue.

The "sulfonylurea derivative" is, for example, tolbutamide, acetohexamide, chlorpropamide, glyclopyramide, tolazamide, gliclazide, glibenclamide, glybuzole, glymidine, etc.

BEST MODE FOR CARRYING OUT THE INVENTION

Figure 1:
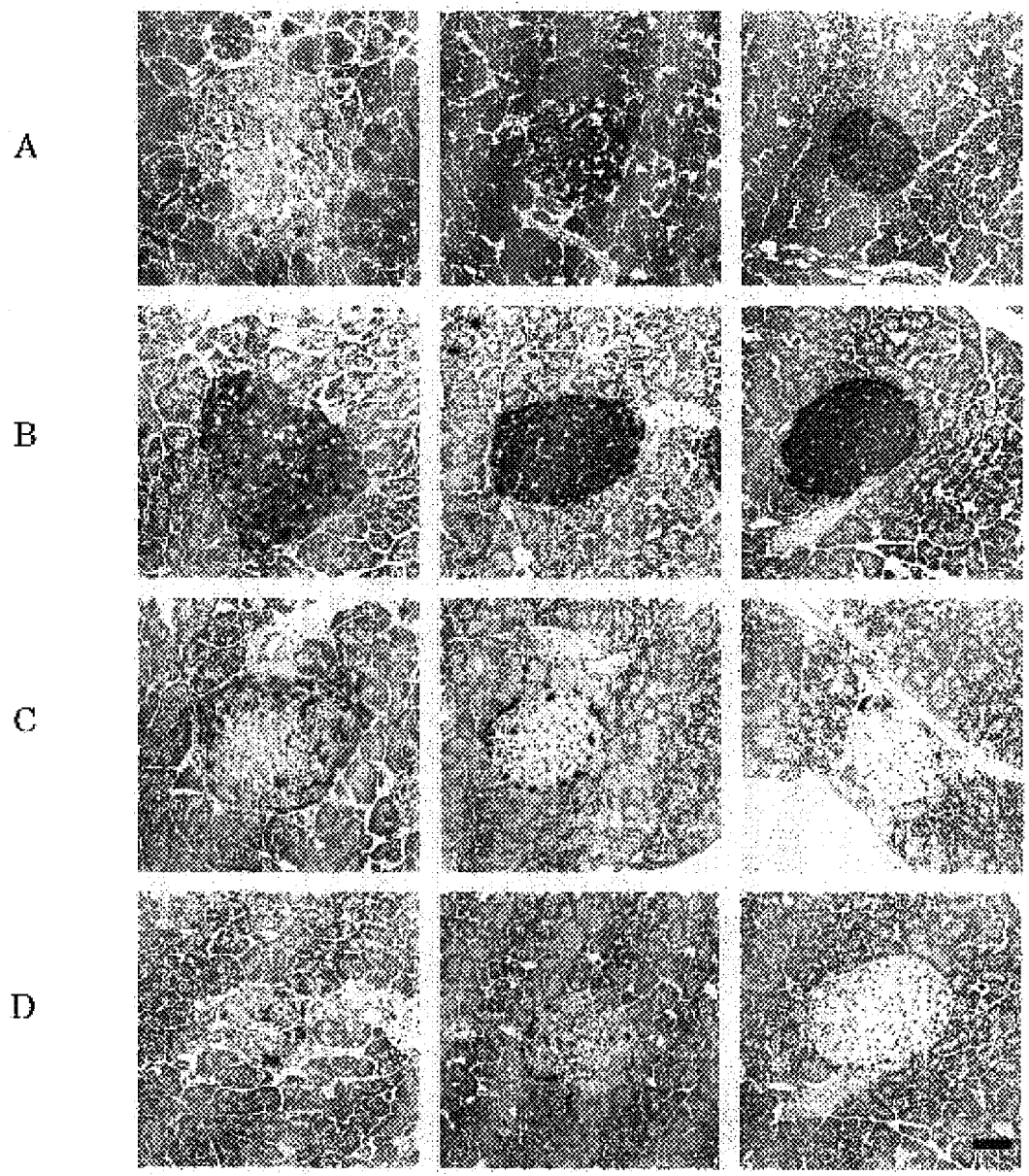
FIG. 1 is a photomicrograph by optical microscope of the stained tissue of pancreas. A: the stained picture by aldehyde fuchsin, B: the stained picture by insulin immune staining, C: the stained picture by glucagon immune staining, and D: the stained picture of somatostatin immune staining. The db/db (vehicle) means diabetic control mice, the db/db (BDNF) means diabetic BDNF-treated mice, and the db/m (normal) means normal control mice.

The neurotrophic factors used as an active ingredient of the present invention may be commercially available ones or can be prepared by the following methods.

The neurotrophic factors used as the active ingredient of the present invention can be any ones prepared by various methods as far as they are purified to such a degree that it could be used as a medicament. The neurotrophic factor can be obtained by cultivating a primary culture cell or an established cell line that can produce the neurotrophic factor, and isolating and purifying it from the culture medium thereof (e.g., culture supernatant, cultured cells). Moreover, a recombinant neurotrophic factor can be obtained by a conventional gene engineering technique, e.g., by inserting a gene encoding a neurotrophic factor into a suitable vector, transforming a suitable host with the recombinant vector, and isolating from a culture supernatant of the resulting transformant. The host cells to be used in the above process are not limited, and may be any conventional host cells which have been used in a gene engineering technique, for example, *Escherichia coli, Bacillus subtilis*, yeasts, mold fungi, plant cells or animal cells.

The neurotrophic factors obtained in the above method include a modified recombinant neurotrophic factor such as ones produced by a deletion of a part of amino acid sequence, or a substitution by other amino acid(s), or an addition of a part of other amino acid sequence, or ones having one or more amino acids at the N-terminus and/or the C-terminus, or ones wherein the sugar chain is deleted or substituted, as far as they exhibit substantially the same activity.

Method for Preparation of BDNF

When a conventional gene engineering technique is employed, BDNF is prepared by inserting a gene encoding BDNF into a suitable vector, transforming a suitable host with the recombinant vector, and isolating it from a culture supernatant of the resulting transformant (cf., Proc. Natl. Acad. Sci. USA, vol. 88, p. 961 (1991); Biochem. Biophys. Res. Commun., vol. 186, p. 1553 (1992)). The gene engineering technique is suitable for production of BDNF of same quality in a large scale. The host cells mentioned above are not limited, but may be any conventional host cells which have been used in a gene engineering technique, for example, *Escherichia coli, Bacillus subtilis*, yeasts, plant cells or animal cells.

Method for Preparation of NT-3

NT-3 can be prepared by expressing in various host cells in the same manner as in the preparation of BDNF. The methods for preparing thereof and the methods for assay thereof are disclosed in Neuron, vol. 4, 767–773 (1990), or JP-A-5-161493 (WO 91/3659).

Method for Preparation of NT-4

NT-4 can be prepared by expressing in various host cells in the same manner as in the preparation of BDNF. The methods for expression of the recombinant NT-4 and the methods for assay thereof are disclosed in Proc. Natl. Acad. Sci. USA, vol. 89, p. 3060–3064 (1992.4), JP-A-7-509600 (WO 93/25684), or JP-A-6-501617 (WO 92/5254).

Method for Preparation of CNTF

CNTF can be prepared in a large scale by expressing in various host cells in the same manner as in the preparation of BDNF. The methods for expression of the recombinant CNTF and the methods for assay thereof are disclosed in Biochimica et Biophysica Acta, vol. 1090, p. 70–80 (1991), J. Neurochemistry, vol. 57, p. 1003–1012 (1991). The methods for preparing the recombinant CNTF and the purification thereof are disclosed in JP-A-4-502916 (WO 90/7341).

The agent for protecting or ameliorating pancreatic cell function, or an agent for protecting or ameliorating pancreatic tissue function, which comprise as the active ingredient a neurotrophic factor, can be administered either parenterally or orally.

The precise dosage and the administration schedule of the above agents of the present invention should vary according to the dosage to be required for each patient, the method for treatment, the disease to be treated, or the degree of necessity, and further according to the diagnosis by a physician. When administered parenterally, the dosage and the frequency of the administration may vary according to the conditions, ages, body weights of patients, and administration routes, but when it is administered subcutaneously or intravenously in the form of an injection, then the daily dosage thereof is in the range of about 1 to about 2500 μg, preferably in the range of about 10 to about 500 μg per 1 kg of the body weight in an adult. When it is administered to the air tract in the form of an aerosol spray, the daily dosage thereof is in the range of about 1 μg to about 2500 μg, preferably in the range of about 10 to about 500 μg per 1 kg of the body weight in an adult. The administration schedule is either continuous daily administration, intermittent administration, or a schedule of combining these methods.

When administered orally, the dosage and the frequency of administration may vary according to the conditions, ages, body weights of patients, and administration routes, and the daily dosage thereof is in the range of about 5 to about 2500 μg, preferably in the range of about 10 to about 1000 μg per 1 kg of the body weight in an adult.

A pharmaceutical composition can be prepared by mixing a neurotrophic factor with a pharmaceutically acceptable non-toxic carrier. When a pharmaceutical composition for parenteral administration (subcutaneous injection, intramuscular injection, or intravenous injection) is prepared, it is preferably in the form of a solution preparation or a suspension preparation. When a pharmaceutical composition for intravaginal administration or rectal administration is prepared, it is preferably in the form of a semi-solid preparation such as cream or suppository. When a pharmaceutical composition for intranasal administration is prepared, it is preferably in the form of a powder, a nasal drop, or an aerosol.

The pharmaceutical composition is administered in the form of a single dosage unit, and can be prepared by any conventional method that is known in the pharmaceutical field such as methods disclosed in Remington's Pharmaceutical Science (published by Mack Publishing Company, Easton, Pa., 1970). An injection preparation may optionally contain as a pharmaceutical carrier a protein derived from plasma such as albumin, an amino acid such as glycin, or a carbohydrate such as mannitol, and additionally a buffering agent, a solubilizer, or an isotonic agent, etc. can be contained. When the present pharmaceutical composition is in the form of an aqueous solution preparation or a lyophilized preparation, it may preferably contain a surfactant such as Tween 80 (registered trade mark), Tween 20 (registered trade mark), etc. in order to avoid aggregation. When the present pharmaceutical composition is a composition for parenteral administration other than an injection preparation, then it may contain distilled water or physiological saline solution, polyalkylene glycol such as polyethylene glycol, an oil derived from plant, hydrogenated naphthalene, etc. For example, a pharmaceutical composition such as a suppository for intravaginal administration or rectal administration may contain as a conventional excipient polyalkylene glycol, vaseline, cacao butter, etc. A pharmaceutical composition for intravaginal administration may contain an absorbefacient such as a bile salt, an ethylenediamine salt, a citrate, etc. A pharmaceutical composition for inhalation may be in the form of a solid preparation, and may contain as an excipient lactose, etc., and a pharmaceutical composition for intranasal drop may be in the form of an aqueous solution or an oily solution.

The present pharmaceutical composition is especially preferable in the form of a formulation by which the present compound can persistently be given to a subject by a single administration for a long term, e.g., for one week or one year, and various sustained release preparations, depot preparations, or implant preparations can be employed. For example, a pharmaceutical composition may contain a neurotrophic factor per se, or a pharmaceutically acceptable salt of a neurotrophic factor of which solubility in body fluid is low. Such pharmaceutically acceptable salts are, for example, (1): an acid addition salt such as phosphate, sulfate, citrate, tartrate, tannate, pamoate, alginate, polyglutarate, naphthalenemono- or di-sulfonate, polygalacturonate, etc., (2): a salt or complex with polyvalent metal cation such as zinc, calcium, bismuth, barium, nickel, etc, or a combination of (1) and (2), for example, a tannic acid zinc salt, etc. A neurotrophic factor is preferably converted into a slightly-water-soluble salt thereof, which is mixed with a gel, for example, aluminum monostearate gel and sesame oil, etc. to give a suitable injection preparation. In this case, especially preferable salt is a zinc salt, a tannic acid zinc salt, a pamoate, etc. Another type of a sustained release injection preparation is ones wherein a neurotrophic factor is preferably converted into a slightly-water-soluble salt thereof, which is further enclosed in a slow-disintegrative non-toxic and non-antigenic polymer such as a polymer or a copolymer of polylactic acid/polyglycolic acid. In this case, especially preferable salt is zinc salt, tannic acid zinc salt, pamoate, etc. In addition, a neurotrophic factor or a slightly-water-soluble salt thereof can be enclosed into a cholesterol matrix or collagen matrix to give a sustained release preparation.

The pharmaceutical preparation for oral administration may be ones which are prepared by microencapsulating a neurotrophic factor or a salt thereof with lecithin, cholesterol, a free fatty acid, or ones which are prepared by enclosing said microcapsules into gelatin capsules, or ones which are prepared by enclosing a neurotrophic factor or a salt thereof in enteric capsules, etc. These preparations may additionally contain, for example, an absorbefacient, a stabilizer, a surfactant, etc.

The agent for protecting or ameliorating pancreatic cell function or the agent for protecting or ameliorating pancreatic tissue function can be administered alone or together with insulin to a patient with pancreatic function disorder. The present agents can prevent pancreatic hypofunction of a patient with pancreatitis or pancreatic cancer, and can enable said patient to easily control the blood glucose level or metabolism. When the present agent is administered together with insulin, the dosage of insulin is in the range of 4 to 100 units/human/day in terms of human insulin, and the daily dosage of a neurotrophic factor, which is administered simultaneously or in advance with insulin, is in the range of about 1 to about 2500 $\mu$g, preferably in the range of about 10 to about 500 $\mu$g per 1 kg of the body weight of an adult.
(Toxicity)

When a neurotrophin, especially BDNF, was administered subcutaneously to rats and cynomolgus monkeys at a dose of 100 mg/kg and 60 mg/kg, respectively, for four weeks, no animal died. With respect to the acute toxicity, BDNF was administered to rats and cynomolgus monkeys at a dose of 200 mg/kg, and no animal died. Therefore, BDNF shows high safety.

The present invention is illustrated by Examples.

EXAMPLE 1

Ameliorating Effects of BDNF on Pancreatic Tissue Picture of Diabetic Animal Model (1) Materials and Method for Experiment Reagents: BDNF was purchased from REGENERON PHARMACEUTICALS, INC. (USA), and used. The other reagents were commercially available ones with the best quality.

Test animals: Male C57 BL/Ksj-db/db Jcl mice (SPF standard) were purchased from Clea Japan, Inc., as a diabetic animal model. Male C57BL/KsJ-db/m Jcl mice (SPF standard) were purchased from Clea Japan, Inc., as a normal mouse. After pre-feeding, the animals were used in the experiment at 11 weeks old. The mice were kept in a room controlled at a temperature of 23±2° C. under a humidity of 55±10%, with an illumination cycle of light on (8:00 to 20:00) and light off (20:00 to 8:00). During the pre-feeding, the animals were freely fed with animal chaw (CE-2, Clea Japan, Inc.) and sterilized tap water.

(2) Preparation of BDNF Solution and Administration Thereof

A BDNF solution was prepared by diluting with a phosphate buffer (10 mM phosphoric acid, 150 mM sodium chloride, pH 7.0±0.2) containing 1% mannitol and 0.01% Tween 80 to a concentration of 20 mg/ml, and used in the experiment. The solution was administered subcutaneously once a day at a dose of 20 mg/kg/day, for 3 weeks.

(3) Preparation of Pancreatic Extract and Measurement of Insulin Content and Glucagon Content Therein After the 3-weeks administration of BDNF, the spleen side of the pancreas was excited, and the weight thereof was measured. The excited tissue was homogenized in an acid-ethanol, and the mixture was allowed to stand at 4° C. overnight. The mixture was centrifuged, and the supernatant was kept at −20° C. The insulin concentration in the extract was assayed by sandwich ELISA (Lewis™ insulin-mouse ELISA kit, Shibayagi Co., Ltd.), and the glucagon concentration in the extract was measured by competitive RIA (glucagon RIA kit, Rinco Research, Ltd.). The contents thereof were calculated from the concentration in the extract and the weight of the tissue. The results are shown in Table 1 and Table 2, respectively.

TABLE 1

| Group | Insulin content (ng/mg of tissue weight) | |
|---|---|---|
| Normal control mouse | 187.7 ± 25.3 | |
| Diabetic control mouse + Vehicle administration | 64.9 ± 21.3 | a |
| Diabetic mouse + BDNF administration | 672.3 ± 130.0 | b c |

TABLE 2

| Group | Glucagon content (ng/mg of tissue weight) | |
|---|---|---|
| Normal control mouse | 1.88 ± 0.36 | |
| Diabetic control mouse + Vehicle administration | 6.87 ± 1.61 | b |
| Diabetic mouse + BDNF administration | 4.08 ± 0.44 | b c | a P < 0.05 vs. Normal control (Turkey's test)
b P < 0.01 vs. Normal Control (Turkey's test)
c P < 0.01 vs. Diabetic mouse + Vehicle administration (Turkey's test)

(4) Tissue Staining of Pancreas

After the 3-weeks administration of BDNF, the duodena side of the pancreas was excised, and fixed with Bouin's solution, and a paraffin block was prepared therefrom by a conventional method. From this paraffin block a section slide of thickness of 3 $\mu$m was prepared, and it was subjected to aldehyde fuchsin staining, insulin immune staining, glucagon immune staining, and somatostatin immune staining.

As a control, the normal mouse and the diabetic mouse were treated, and the pancreas thereof was subjected to tissue staining in the same manner as above.

As to the stained tissues obtained in the above, a photomicrograph by an optical microscope was obtained (size bar indicates 200 μm). These pictures are shown in FIG. 1. In FIG. 1, A is the stained picture by aldehyde fuchsin staining, B is the stained pictures by insulin immune staining, C is the stained pictures by glucagon immune staining, and D is the stained pictures by somatostatin immune staining. The db/db (vehicle) indicates the diabetic control mouse, and the db/db (BDNF) indicates the diabetic BDNF-treated mouse, and the db/m (normal) indicates the normal control mouse.

(5) Results (i) Amelioration of Insulin and Glucagon Contents in Pancreas by BDNF Administration As is apparent from the results as shown in the above Table 1 and Table 2, when comparing with the normal control mice, the insulin content in pancreas of the diabetic control mice was reduced to about 25%, while the glucagon content in pancreas thereof was about 3 times higher. On the contrary, the insulin content in pancreas of the diabetic mice to which BDNF has been administered for 3 weeks was increased to about 10 times as that of the diabetic control mice. On the other hand, the glucagon content in pancreas of said BDNF-treated mice was reduced to about 50% of that of the diabetic control mice. From these results, it was confirmed that BDNF can normalize the pancreatic function of diabetic mouse by increasing the insulin content in pancreas and reducing the glucagon content in pancreas.

(ii) Histological Amelioration of Pancreatic Tissue by BDNF Administration

From the results of aldehyde fuchsin staining as shown in FIG. 1, the apparent decrease of insulin granules was observed in the pancreas of the diabetic control mouse, as compared with the pancreas of a normal mouse. On the other hand, the distinguished re-granulation of insulin granules was observed in the BDNF-treated group. The similar result was also obtained in the stained pictures by insulin immune staining. In the glucagon immune staining and the somatostatin immune staining, the internalization of glucagon-positive cells and somatostatin-positive cells was observed in the diabetic control mouse. On the other hand, these cells exist in the marginal part of Langerhans islet of the BDNF-treated group, as a similar manner as in the normal control mouse. Thus, it was indicated that the amelioration of pancreatic function by BDNF is mediated not only by the increase in insulin content in insulin positive cells but also by the normalization of the glucagon positive cell function.

EXAMPLE 2

Figure 3:
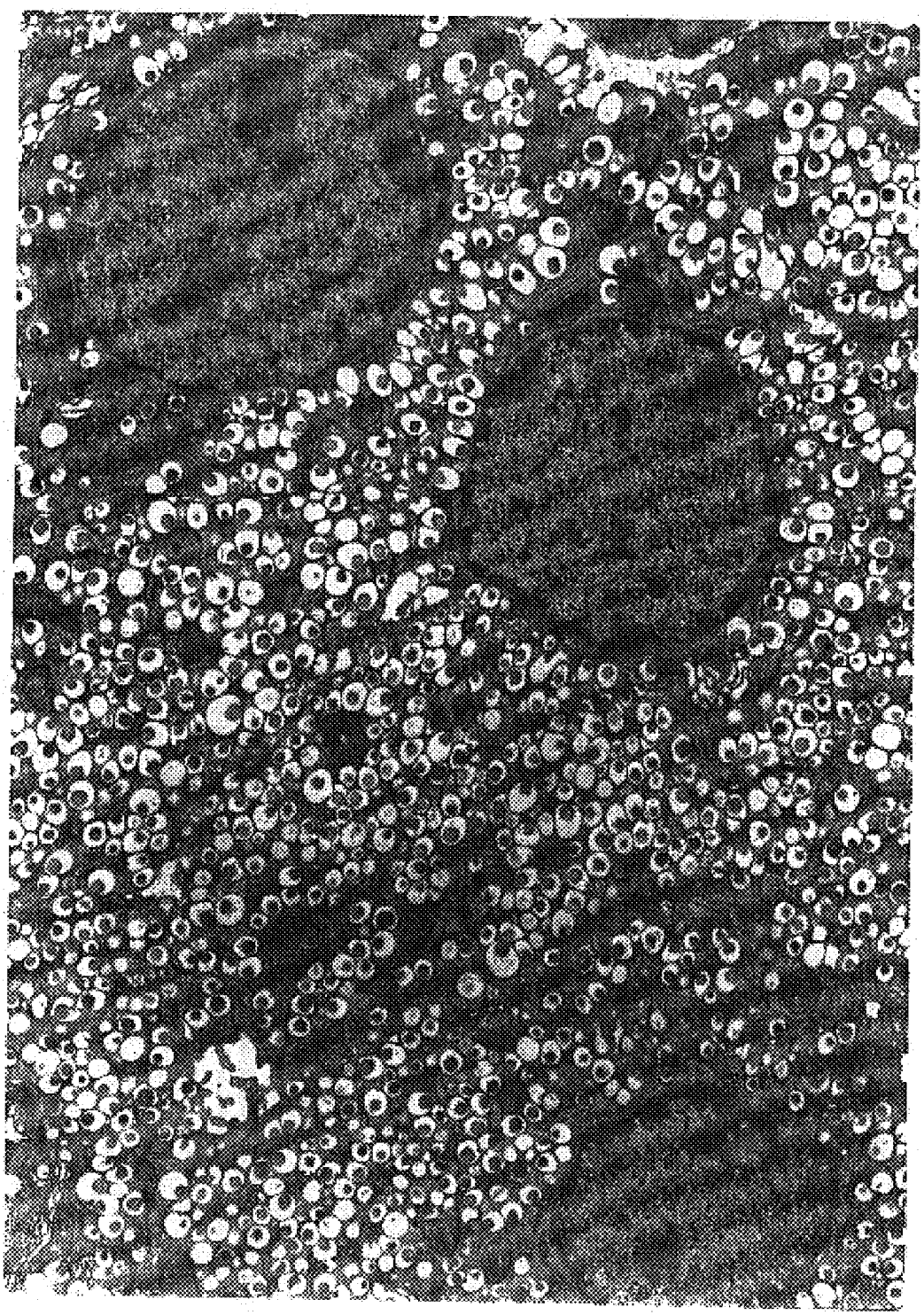
FIG. 3 is an electron micrography (magnification: 8300) of pancreatic B cells of BDNF-treated mice.
Figure 6:
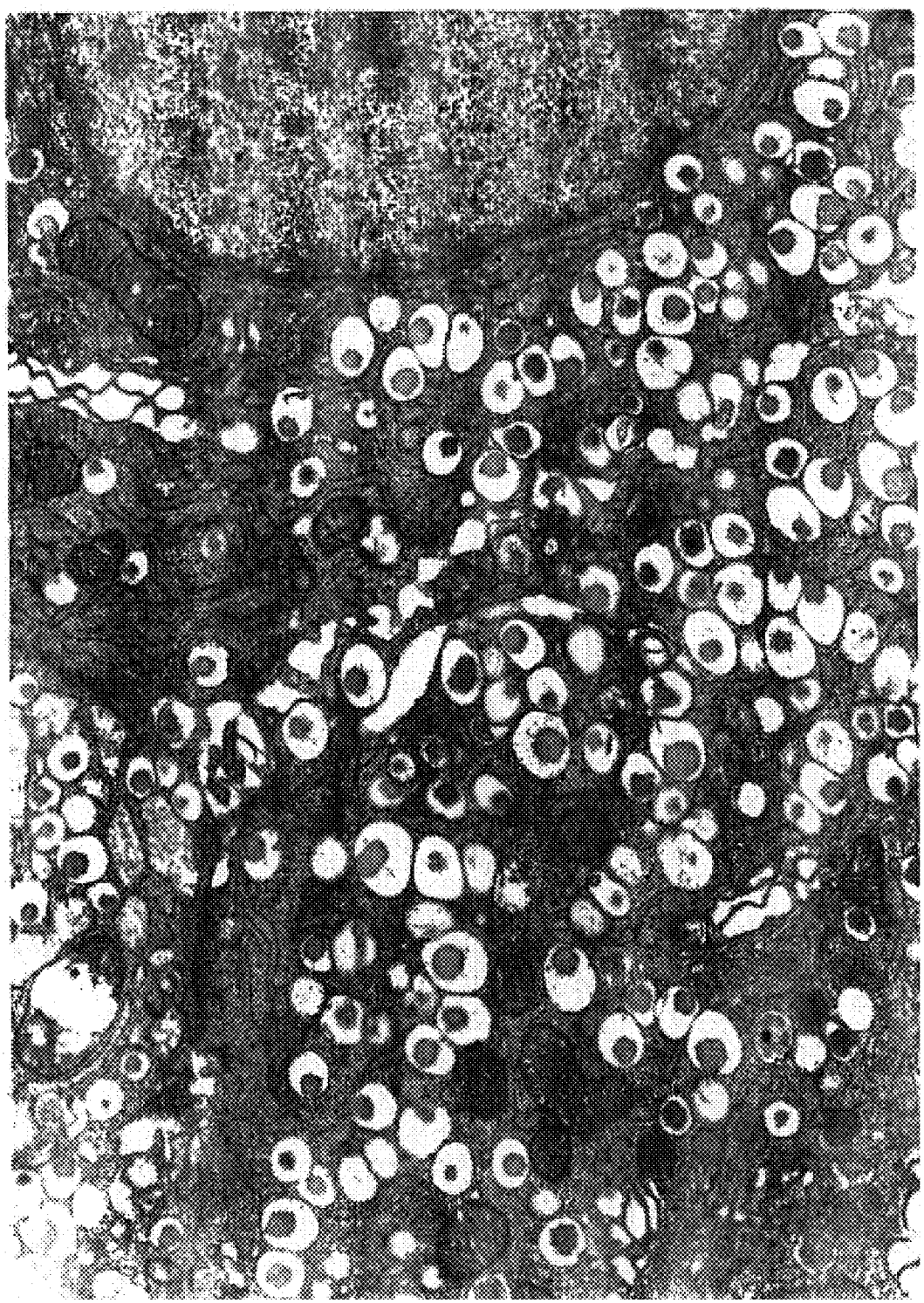
FIG. 6 is an electron micrography (magnification: 16000) of pancreatic B cells of BDNF-treated mice.

Examination of Langerhans Islet B Cells by Electron Microscopy (1) According to the procedure of Example 1, BDNF was administered to db/db mice of 8 weeks old for 6 weeks, and the spleen side of the pancreas thereof was excised and pre-fixed with 2.5% glutaraldehyde fixative, and further post-fixed with 2% osmic acid fixative, dehydrated, and embedded in an epoxy resin. The ultrathin section was stained with uranium acetate and lead citrate, and the Langerhans islet B cells were examined by a transmission electron microscope (JEM 1200 EXII, JEOL Ltd.) (magnification: 8300 and 16000). The pictures thereof are shown in FIG. 3 and FIG. 6, respectively.

Figure 4:
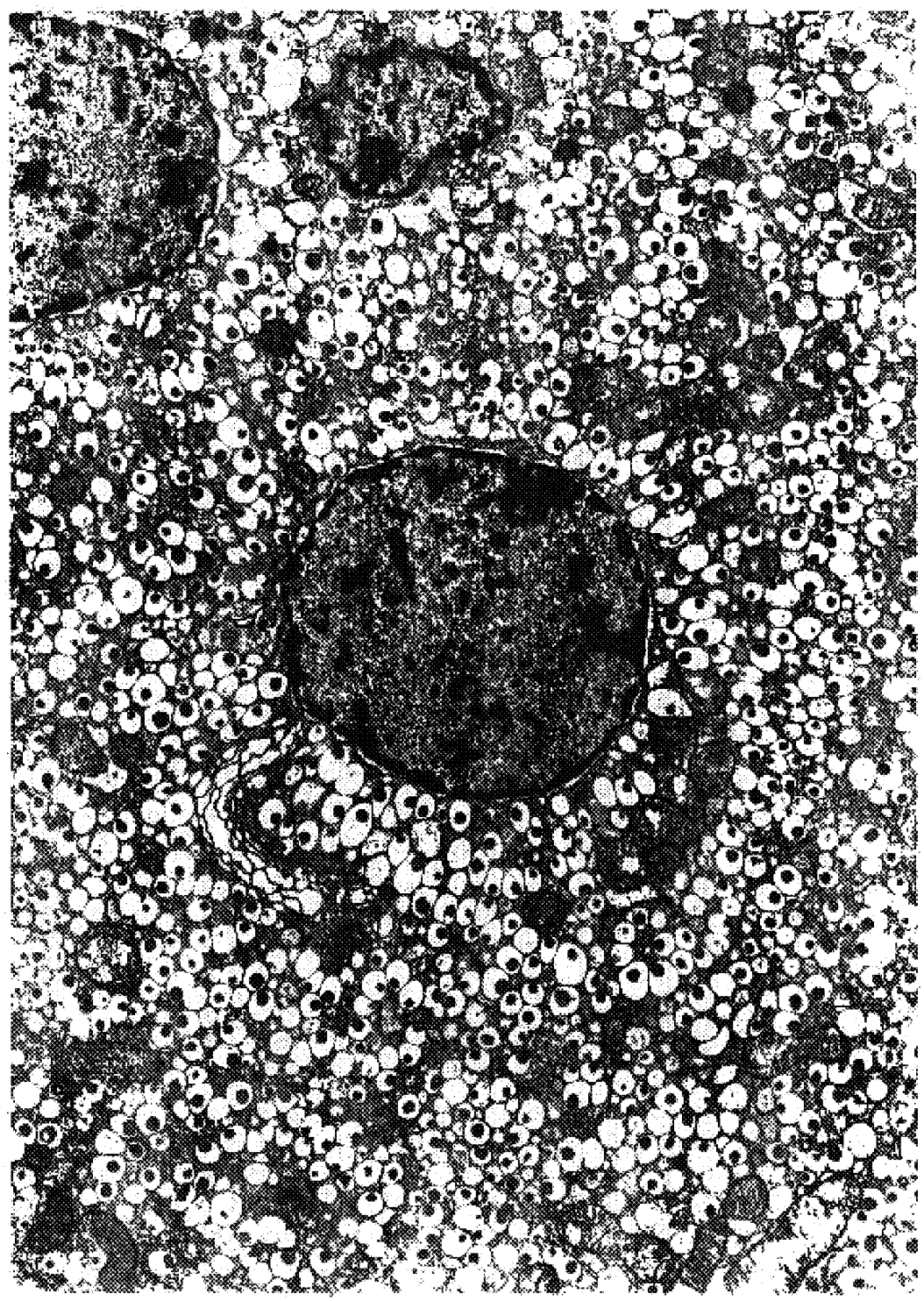
FIG. 4 is an electron micrography (magnification: 8300) of pancreatic B cells of normal mice.
Figure 7:
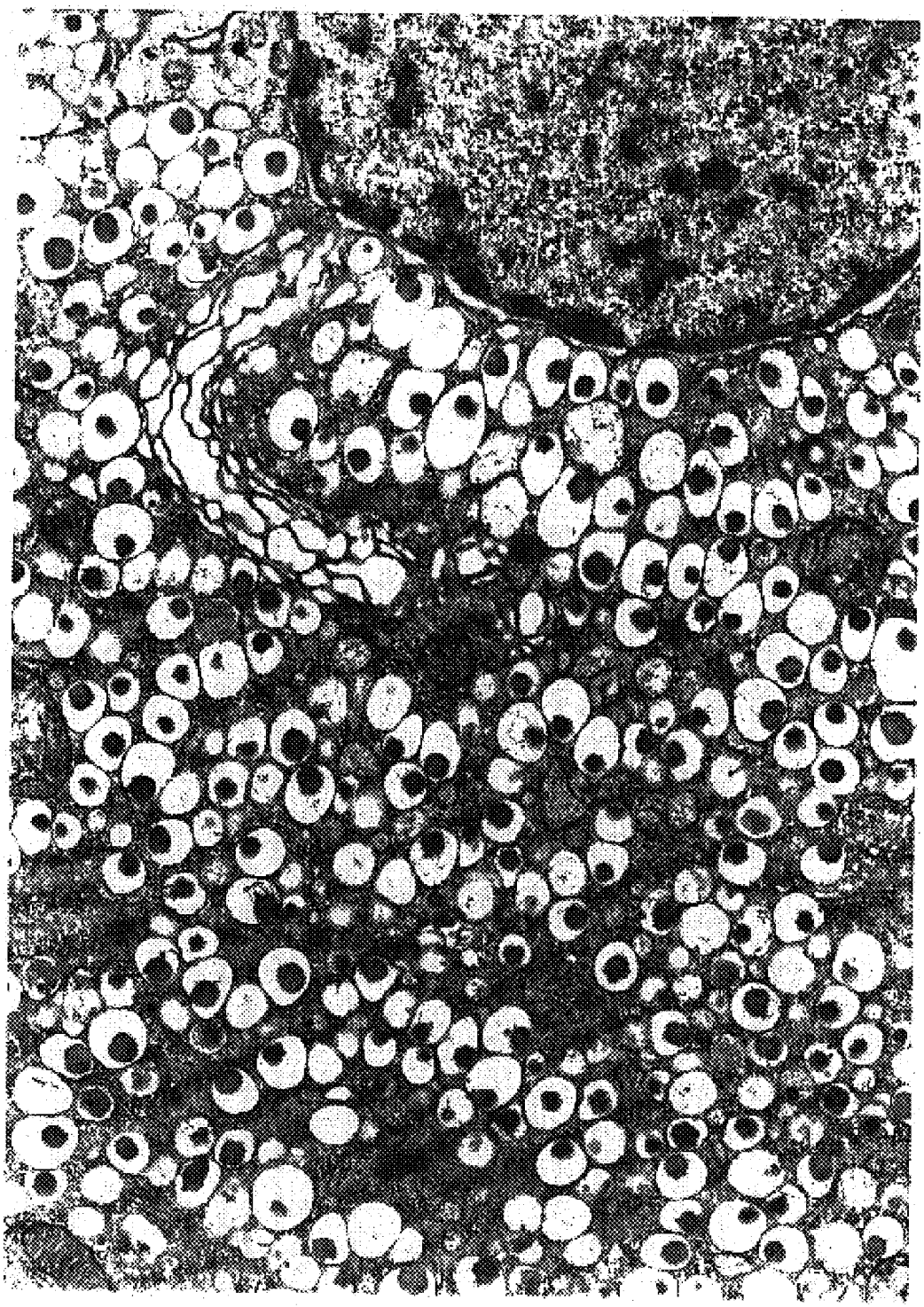
FIG. 7 is an electron micrography (magnification: 16000) of pancreatic B cells of normal mice.

As a normal control animal, C57 BL/6N mice (SPF standard) were purchased from Charles River Japan Inc., and they were used at 14 weeks old for sampling without any treatment. In the same manner as in the above BDNF-treated mice, the Langerhans islet B cells were examined by a transmission electron (magnification: 8300 and 16000). The pictures thereof are shown in FIG. 4 and FIG. 7, respectively. As a diabetic control mouse, the same diabetic mice as used in Example 1 were used, and they were treated in the same manner. The electron micrographs (magnification: 8300 and 16000) are shown in FIG. 2 and FIG. 5, respectively.

(2) Results

As is shown in FIG. 4 and FIG. 7, there were multiple insulin secretory granules in the cytoplasm of the B cells of the normal control C57BL mice, and it was observed that mitochondria and Golgi apparatus were disseminated therein, while rough endoplasmic reticulum was scarce and not clear.

Figure 2:
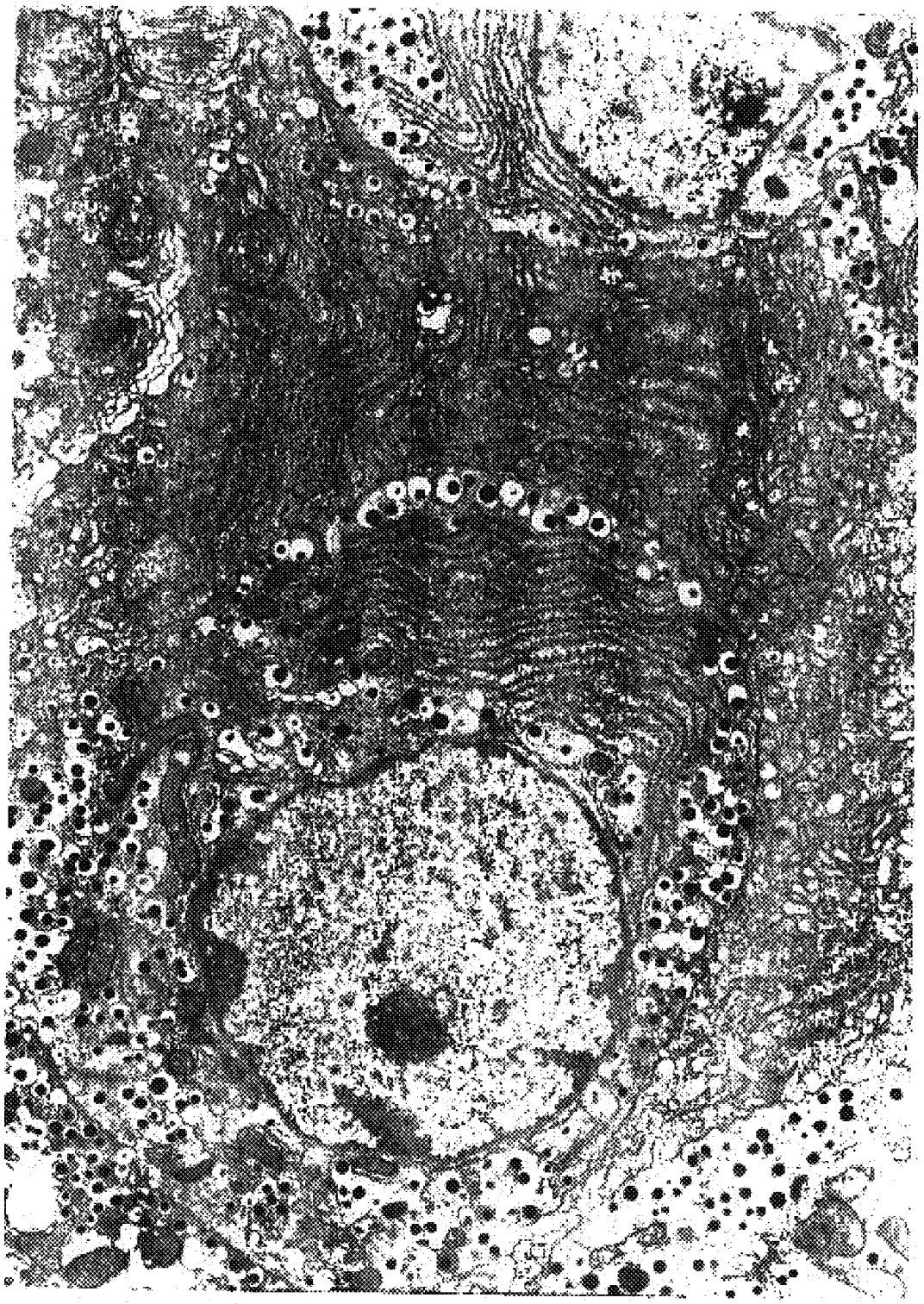
FIG. 2 is an electron micrography (magnification: 8300) of pancreatic B cells of diabetic control mice.
Figure 5:
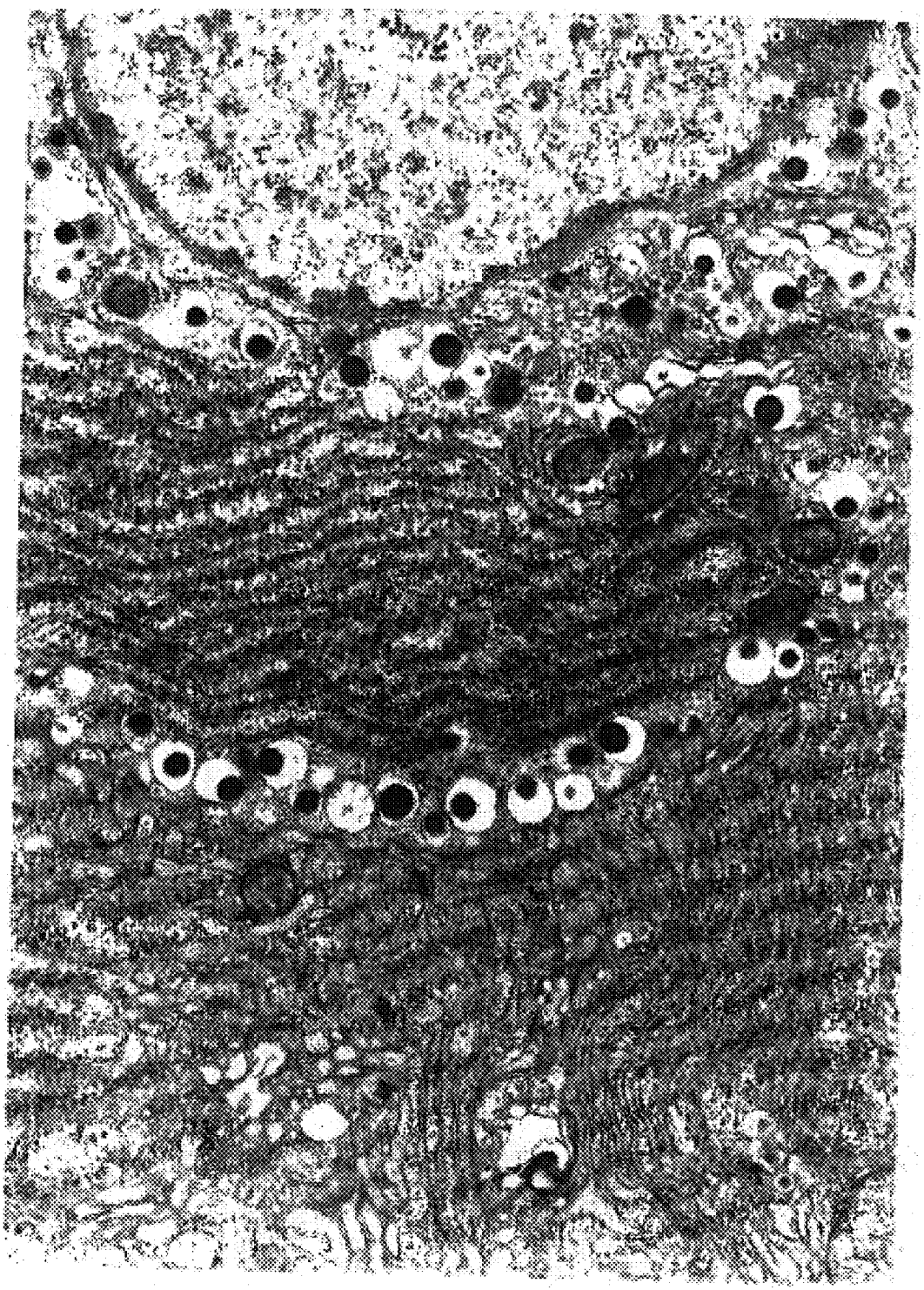
FIG. 5 is an electron micrography (magnification: 16000) of pancreatic B cells of diabetic control mice.

On the other hand, as shown in FIG. 2 and FIG. 5, there was an apparent decrease in secretory granules in the diabetic control db/db mice. In addition, the increase in rough endoplasmic reticulum, the enlargement of Golgi apparatus, and the jumboizing (hypertrophy) of mitochondria were observed, and they indicated the hypofunction of pancreatic B cell endocrine.

On the contrary, as shown in FIG. 3 and FIG. 6, the reaccumulation of secretory granules was observed in the BDNF-treated db/db mice. In addition, the increase in rough endoplasmic reticulum, the enlargement of Golgi apparatus, and the jumboizing of mitochondria were hardly observed, and the tissue electron micrography thereof was similar to that of the normal C57BL mice.

From the above results, it was confirmed that the pancreatic endocrine function of db/db mice is normalized by BDNF administration.

INDUSTRIAL APPLICABILITY

The present agent comprising as the active ingredient a neurotrophic factor exhibits an ameliorating effect on pancreatic function disorder being induced by various causes, and can protect the pancreatic cells or tissues, and further exhibits an ameliorating effects on the hypofunction of damaged pancreatic cells or tissues, and it is useful as an agent for protecting or ameliorating pancreatic function disorder.

What is claimed is:

1. A method of protecting pancreatic cell function or of ameliorating hypofunction of pancreatic cells in a subject presenting type II diabetes and a defect in insulin secretion, which comprises administering a brain-derived neurotrophic factor to the subject.

2. A method of protecting pancreatic tissue function or of ameliorating hypofunction of pancreatic tissues in a subject presenting type II diabetes and a defect in insulin secretion, which comprises administering a brain-derived neurotrophic factor to the subject.

3. The method according to claim 1, wherein the pancreatic cell is selected from the group consisting of B cells (β cells), A cells, (α cells), D cells (δ cells) of pancreatic Langerhans islet and mixtures thereof.

4. The method according to claim 2, wherein the pancreatic tissue is pancreatic Langerhans islet.

5. A method of ameliorating pancreatic endocrine function disorder in a subject, which comprises administering an effective amount of a brain-derived neurotrophic factor to the subject.

6. A method of protecting pancreatic cell function or of ameliorating hypofunction of pancreatic cells or tissues in a subject exhibiting a disorder of pancreatic endocrine or exocrine hormone secretion, which comprises administering an amount of a brain-derived neurotrophic factor to the subject effective to protect pancreatic cell function or ameliorate hypofunction of pancreatic cells or tissues.

7. The method of claim 6 in which the pancreatic cell hypofunction is ameliorated, the hypofunction is hypofunction of islet cells and the subject exhibits a defect in insulin secretion.

8. The method of claim 6, in which the administration of the brain-derived neurotrophic factor provides re-granulation of insulin granules.

* * * * *